(12) United States Patent
Nelson et al.

(10) Patent No.: US 8,859,838 B1
(45) Date of Patent: Oct. 14, 2014

(54) PROTECTIVE COVER

(76) Inventors: Clare Nelson, Cranston, RI (US); James Nelson, Cranston, RI (US)

( * ) Notice: Subject to any disclaimer, the term of this patent is extended or adjusted under 35 U.S.C. 154(b) by 385 days.

(21) Appl. No.: 13/100,359

(22) Filed: May 4, 2011

Related U.S. Application Data

(60) Provisional application No. 61/332,327, filed on May 7, 2010.

(51) Int. Cl.
*A61F 15/00* (2006.01)

(52) U.S. Cl.
USPC .......................... 602/44; 604/378; 604/385.24

(58) Field of Classification Search
USPC .......................... 602/44; 604/263, 378, 385.24
See application file for complete search history.

(56) References Cited

U.S. PATENT DOCUMENTS

| | | | |
|---|---|---|---|
| 3,106,718 A | 10/1963 | Raab | |
| 5,036,838 A * | 8/1991 | Sherman | 602/44 |
| 5,814,003 A | 9/1998 | Knox et al. | |
| 6,526,981 B1 | 3/2003 | Rozier et al. | |
| 2004/0077998 A1* | 4/2004 | Morris | 604/93.01 |
| 2007/0078364 A1* | 4/2007 | Belcher | 602/42 |
| 2007/0083163 A1 | 4/2007 | Rydell | |

* cited by examiner

*Primary Examiner* — Kevin C Sirmons
*Assistant Examiner* — Deanna K Hall
(74) *Attorney, Agent, or Firm* — Salter & Michaelson

(57) ABSTRACT

A sheath for covering an intravenous device to shield the device from a patient's skin. The sheath includes a layer of a soft woven material; and a thin layer of a plastic material formed on an inner surface of the soft woven material to form, with said soft woven material, a pliable wrap meant to be disposed about the intravenous device for shielding the patient's skin from the intravenous device. The pliable wrap has inner and outer surfaces, top and bottom ends, and respective sides. An elastic member is secured to at least one of the top and bottom surfaces of the pliable wrap to provide a gathered area surrounding the intravenous device at at least one end thereof. A fastening member is secured between the respective sides of the pliable wrap to extend in a closed manner about the intravenous device.

5 Claims, 5 Drawing Sheets

PROTECTIVE COVER

RELATED APPLICATION

The present application claims priority to U.S. Provisional Application Ser. No. 61/332,327 filed on May 7, 2010. The content of all of the aforementioned application is hereby incorporated by reference herein in its entirety.

FIELD OF THE INVENTION

The present invention relates in general to a protective cover or sheath. More particularly, the present invention relates to a protective cover or sheath that is adapted for use about an intravenous or the like device. This sheath or cover is meant to shield such devices from a patient's skin.

BACKGROUND OF THE INVENTION

A central venous access device, or CVAD, is considered to be a relatively broad term that includes many types of catheters (thin and flexible hollow tubes) that are extensively used in the medical profession. These devices are for insertion into and positioning within a vein in the body to deliver therapeutics to the bloodstream. These devices may administer antibiotics, chemotherapeutic drugs, total parenteral nutrition and for providing hemodialysis and plasmapheresis. These devices can remain in place for a period as briefly as a day, or for much longer periods of weeks or possibly even months.

A frequently used CVAD is a catheter arrangement using a thin, flexible tube with a clamp and access cap that dangles at the end of the catheter. Particularly the distal end of the device is in constant with the patient's skin. This frequent contact can be uncomfortable, particularly when the clamp and/or cap is caused to press against the patient's skin during normal patient movements.

For one form of a cuff, refer to the Rydell U.S. Publication No. 2007/0083163. This publication describes a cuff for use with an intravenous line, tubing and associated dressing for patients. However, the IV cuff that is described in this publication is meant for engagement with a patient's limb such as the arm or leg and is sized so that the circumference thereof is less than the circumference of the arm so that a tensile force holds the cuff in place. Thus, this is a far more restrictive arrangement.

Accordingly, it is an object of the present invention to provide an improved protective cover or sheath that is formed as a pliable wrap meant to be disposed about the intravenous device for shielding the patient's skin from the intravenous device. Thus, in accordance with the present invention, the protective cover or sheath covers the intravenous device rather than the patient's limb.

SUMMARY OF THE INVENTION

To accomplish the foregoing and other objects, features and advantages of the present invention there is provided a sheath for covering an intravenous device to shield the device from a patient's skin. The sheath comprises a layer of a soft woven material; and a thin layer of a plastic material formed on an inner surface of the soft woven material to form, with said soft woven material, a pliable wrap meant to be disposed about the intravenous device for shielding the patient's skin from the intravenous device. The pliable wrap has inner and outer surfaces, top and bottom ends, and respective sides. An elastic member is secured to at least one of the top and bottom surfaces of the pliable wrap to provide a gathered area surrounding the intravenous device at at least one end thereof. A fastening member is secured between the respective sides of the pliable wrap to enable the wrap to extend in a closed manner about the intravenous device.

In accordance with other aspects of the present invention the soft woven material may comprise a cotton flannel, a soft woven wool, and may be of a synthetic material; the thin layer may comprise a polyurethane layer; the polyurethane layer may have a thickness on the order of one millimeter; when the pliable wrap is closed the respective ends thereof may be secured so that the wrap is tubular in form with the ends being both gathered; including a separate elastic member secured at both top and bottom ends; wherein, when the pliable wrap is closed the plastic layer is against the intravenous device and the layer of a soft woven material is against a skin surface; the elastic member may comprise an elastic band having a length, in its relaxed state, that is less than the width of the pliable wrap, the elastic band stretched and secured by stitching to an edge at at least one end of the pliable wrap; including opposite end folds that are heat sealed; including opposite side folds that are heat sealed; the fastening member may comprise a hook and loop combination attached at the respective side folds; and the elastic member is disposed within at least one of the end folds.

In another version of the present invention there is provided a method of forming a sheath for covering an intravenous device to shield the device from a patient's skin, said method comprising the steps of: providing a layer of a soft woven material; providing a thin layer of a plastic material; forming the thin layer of a plastic material on an inner surface of the soft woven material to form, with said soft woven material, a pliable wrap meant to be disposed about the intravenous device for shielding the patient's skin from the intravenous device, the pliable wrap having inner and outer surfaces, top and bottom ends, and respective sides; providing an elastic member; securing the elastic member to at least one of the top and bottom surfaces of the pliable wrap to provide a gathered area surrounding the intravenous device at at least one end thereof; and securing between the respective sides of the pliable wrap to extend in a closed manner about the intravenous device.

In accordance with other aspects of the method of the present invention, when the pliable wrap is closed the respective ends thereof are secured so that the wrap is tubular in form with at least one end being gathered; including providing a separate elastic member secured at both top and bottom ends; wherein, when the pliable wrap is closed the plastic layer is against the intravenous device and the layer of a soft woven material is against a skin surface; and wherein the thin layer of a plastic material may include applying the thin layer by any one of coating, depositing, or spraying.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which.

DETAILED DESCRIPTION

Figure 5:
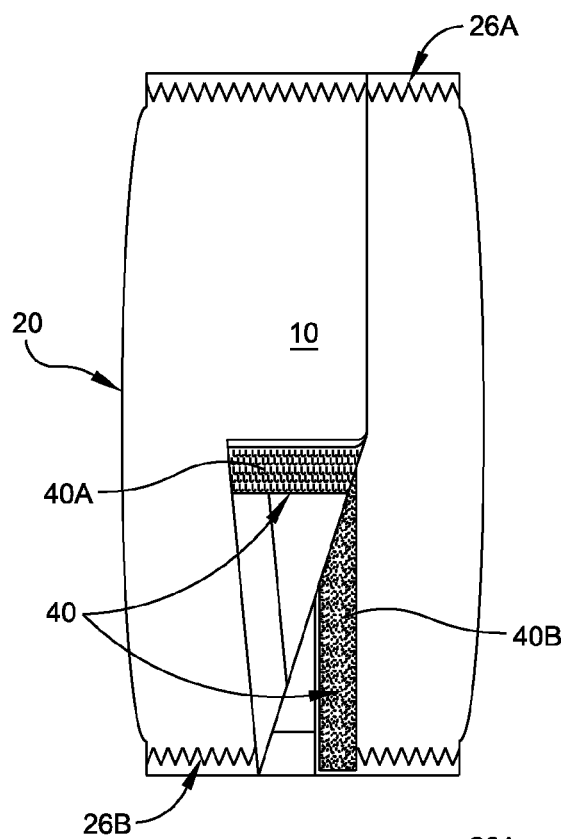
FIG. 5 is a side elevation view of the protective cover in its closed tubular condition and illustrating the hook and loop fastening arrangement.
Figure 6:
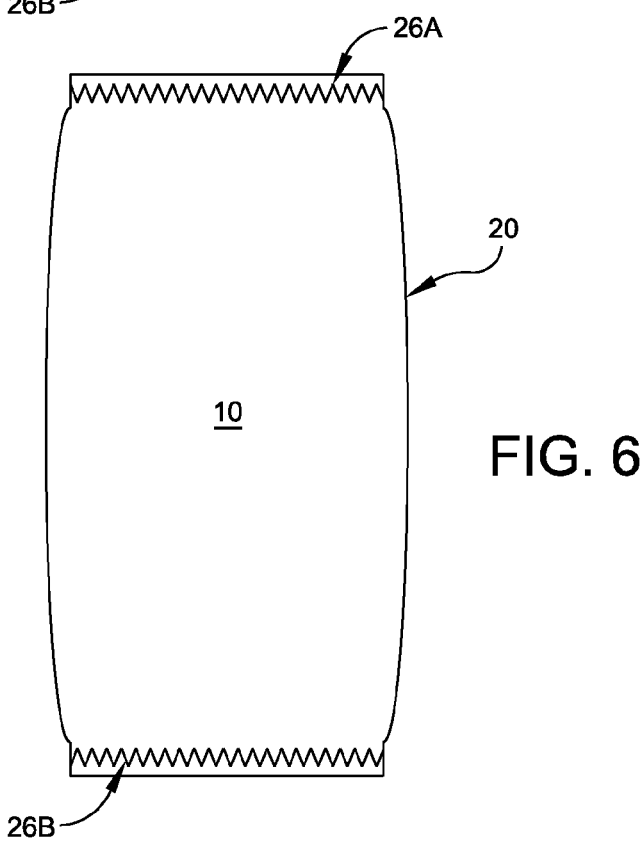
FIG. 6 is a side elevation view showing the protective cover completely closed.
Figure 7:
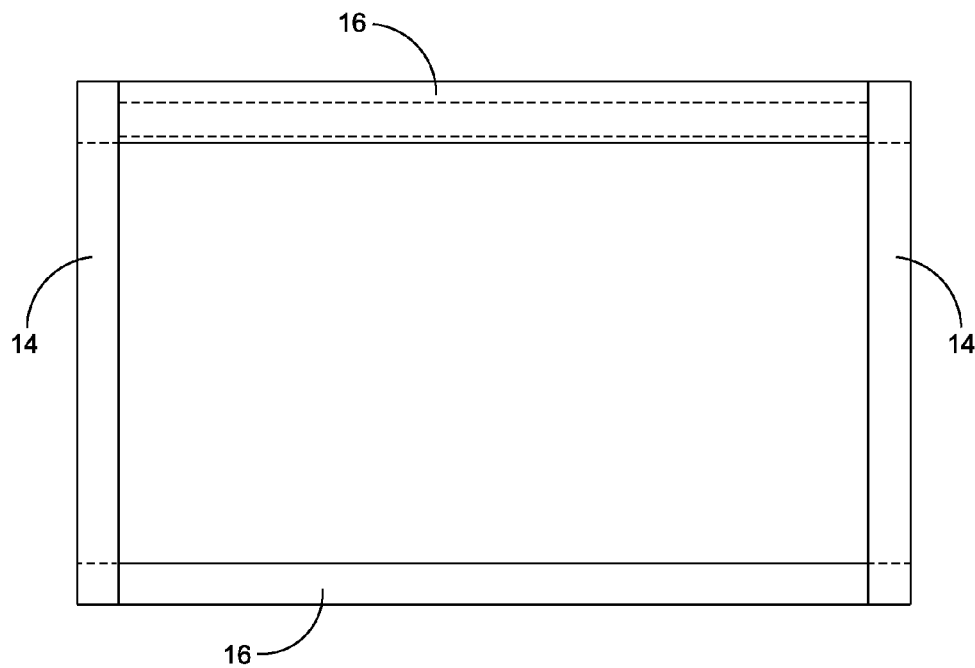
FIG. 7 is a plan view similar to that shown in FIG. 2 for a smaller version of the protective cover.
Figure 8:
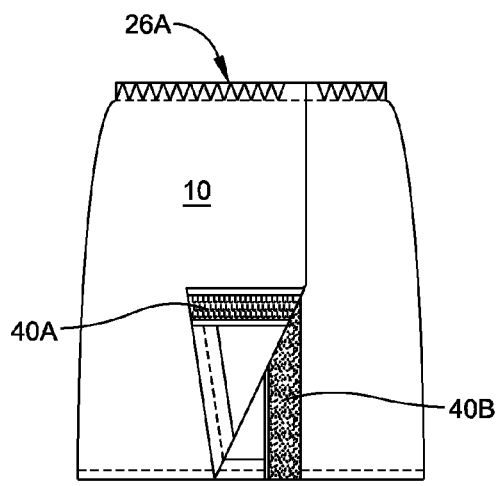
FIG. 8 is a side elevation view like that depicted in FIG. 5 but for the version for FIG. 7.
Figure 9:
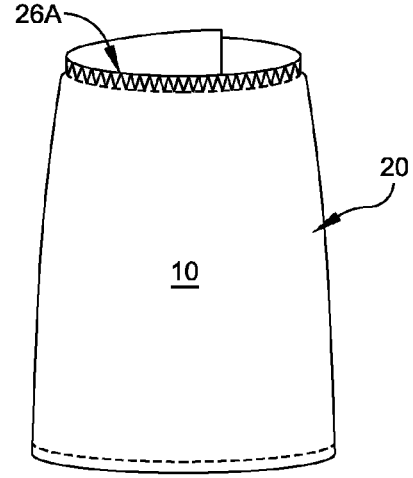
FIG. 9 is a perspective view of the version of FIG. 7 in its closed position.
Figure 10:
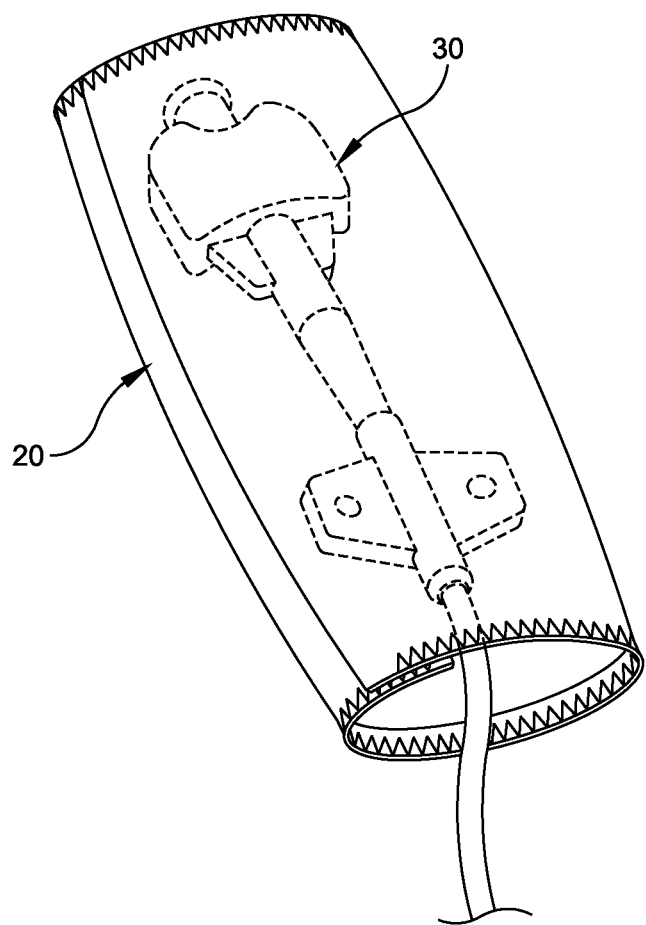
FIG. 10 illustrates the pliable wrap of the present invention as disposed about a CVAD structure.

The protective cover or sheath of the present invention is meant to be wrapped about the hard plastic clamp and/or cap, as is illustrated in FIG. 10. The cotton base material is meant to provide a comfortable outer surface pressed against the patient's skin. In the following drawings there are two styles of pliable wrap that are disclosed. FIGS. 1-6 illustrate a larger wrap version and FIGS. 7-9 illustrate a smaller wrap version. In the larger version elastic members appear at both top and bottom sides of the wrap while in the smaller version illustrated in FIGS. 7-9 only one elastic member is employed at the top of the wrap. In either version, the wrap is meant to be formed into a closed shape such as illustrated in FIG. 9. Refer also to FIG. 10 which shows the wrap in place about the CVAD equipment.

The protective cover of the present invention is comprised of a layer of a soft woven material 10 in combination with a thin layer of a plastic material 12 that is essentially formed on an inner surface of the soft woven material to form, with the soft woven material, a pliable wrap 20 that is meant to be disposed about the intravenous device for shielding the patient's skin from the intravenous device. FIG. 10 schematically illustrates the intravenous device at 30.

The soft woven material layer 10 may be comprised of a cotton or wool flannel. This layer may also be constructed of a soft synthetic material. The thin layer of the plastic material 12 is preferably a thin layer of polyurethane. The polyurethane layer or lining is intended to provide an impervious liner and it can be sterilized using gamma radiation sterilization which is a preferred sterilization method. A preferred form of these layers is 100 percent cotton flannel blend material for the layer 10 and, as indicated previously, a thin polyurethane film layer for layer 12. When the layers are formed in a wrap, as illustrated in FIG. 10, only the inside of the cotton flannel layer is coated. The exterior is not coated and thus provides a soft texture side that enables the covers intended purpose as a comfortable covering over the harsh plastic clamp and/or cap construction. The pliable wrap of the present invention is also constructed so as to be, not only quite comfortable, in its positioning over the CVAD equipment, but also can be easily placed into position and removed if necessary.

Now, in connection with the larger version of the wrap as illustrated in FIGS. 1-6, the cotton flannel 10 is coated on one side with preferably a one mm polyurethane film 12 and is cut into five inch squares. The left and right sides are folded approximately ⅜ inch and heated to allow the folded piece to adhere. In this regard, refer to the plan view of FIG. 2 as well as the cross-sectional view of FIG. 3 that illustrates the fold at 14. A heat press technique may be used to provide the fold at 14 with pressure being applied in the direction of arrow 15. A strip of hook and loop material 40 is used. These respective hook and loop strips 40A, 40B may be approximately 4¼ inch in length by ¼ inch thick. The left (hook) and right (loop) fasteners are secured to the cover by an adhesive that is applied to the back of the hook and loop material, usually provided by the manufacturer of the hook and loop material.

Figure 1:
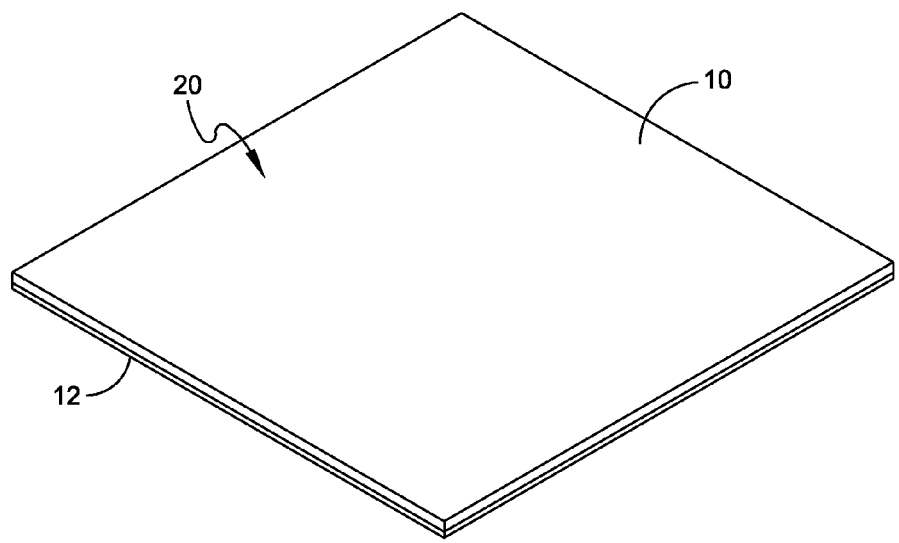
FIG. 1 is a perspective view of the protective cover constructed in accordance with the principles of the present invention and shown in its unwrapped state.
Figure 2:
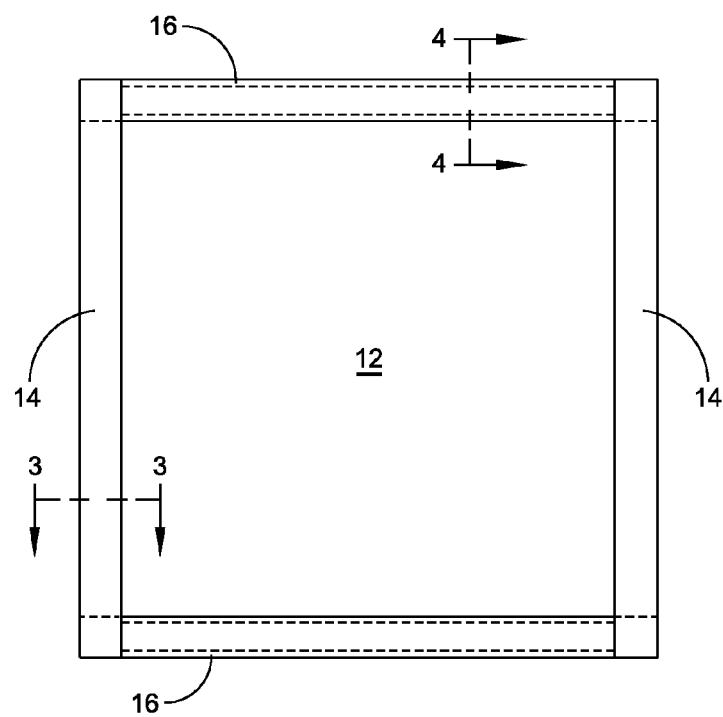
FIG. 2 is a plan view of the cover of FIG. 1 depicting the folds on top, bottom and side edges.
Figure 3:
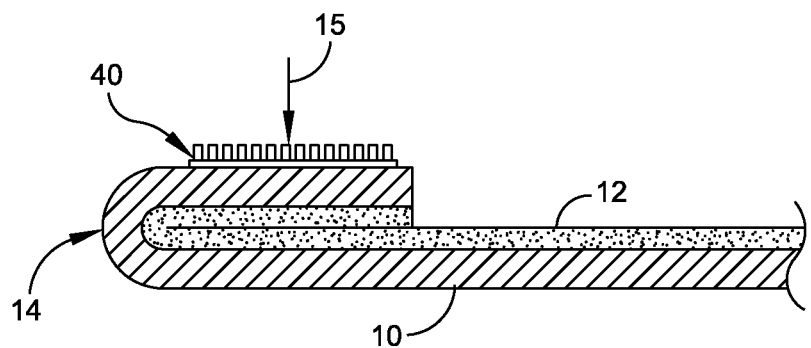
FIG. 3 is a cross-sectional view taken along line 3-3 of FIG. 2 showing the cross-section through a side fold for supporting a fastening member.
Figure 4:
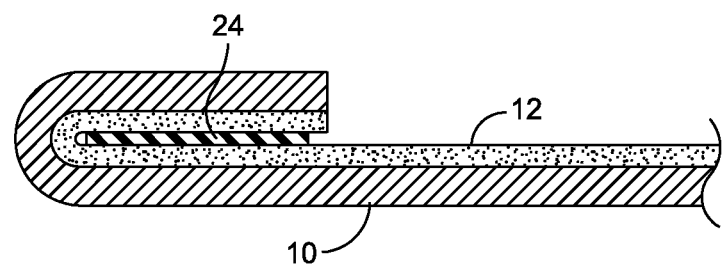
FIG. 4 is a cross-sectional view taken along line 4-4 of FIG. 2 illustrating a cross-section in the area of the elastic member.

In addition to the ⅜ inch fold 14 at the opposite respective sides, there is also provided a top fold and a bottom fold illustrated at 16 in FIG. 2. These folds are also approximately ⅜ inch in width. The fold 16 is disposed over an elongated piece of elastic material that is approximately 10 to 20 mm thick, ¼ inch wide and 3¼ to 3½ inch long. This is illustrated in the drawings by the elastic band 24. The elastic band 24 is meant to be stretched to cover the full width at the top and bottom, namely to approximately 4½ inches. Once stretched, each of the elastic bands 24 is sewn in place to create a gathering at the top and bottom of the cover. Refer to FIGS. 5 and 6 showing the top gathering 26A and the bottom gathering 26B.

Reference is now made to an alternate embodiment of the invention illustrated in FIGS. 7-9 wherein the wrap is of a smaller size and has a gathering only at the top end thereof. In this embodiment the same reference numbers are used as previously described in connection with FIGS. 1-6. Thus, in FIGS. 7-9 the cotton flannel is coated on one side with a preferred one mm polyurethane film and laser cut into rectangles that are 5 inches by 3 inches. The left and right sides are folded approximately ⅜ inch over and heated to allow the folded piece to adhere. A strip of hook and loop material approximately 2⅜ inch in length by ¼ inch thick is attached to the left (hook) and right (loop) inside of the cover using an adhesive that is applied to the hook and loop usually by the manufacturer of the material. The top edge is folded over approximately ⅜ inch as illustrated in FIG. 7. This folding is over a length of elastic band material that is approximately 10 to 20 mm thick, ¼ inch wide and 3¼ to 3½ inch long. The elastic is stretched to cover the width of the top and is sewn to allow a gathering at the top as illustrated at 26A in FIGS. 8 and 9.

In accordance with the manufacturing process of the present invention, it is noted that the soft woven material is coated on one side with the plastic film. Once the material is coated, the material is cut into squares or rectangles depending upon the size of the cover desired. This cutting may be accomplished by laser cutting or by other known cutting techniques. The left and right sides are then heat sealed and the respective hook and loop strips are attached to the cover over the folds. After the application of the hook and loop material to the sides, then the elastic is sewn into the cover. In the first embodiment an elastic is sewn at both the top and bottom and in the second embodiment an elastic is sewn into the fold only at the top.

The cover of the present invention is effective in covering the clamps or caps on a central venous access device with the intention of providing a comfortable cover to reduce the discomfort that may occur as a result of the hard plastic clamps or caps rubbing against the patient's skin. Only the soft woven side of the pliable wrap is exposed to the patient's skin and the side coated with the more solid plastic film is on the interior side against the catheter clamp and/or cap. The more rigid plastic side of the wrap is thus not intended to be exposed to the patient's skin. The fastening member is intended to enable the cover to be formed into its closed shape such as illustrated in FIGS. 9 and 10.

The pliable wrap of the present invention is preferably meant to be manufactured relatively inexpensively. It is meant to be disposable for only single usage. This pliable wrap is relatively inexpensive to manufacture. It can be discarded even during use such as if it becomes wet or soiled. It can also be removed, disposed of and replaced when dressing or changing the IV tubing.

Having now described a limited number of embodiments of the present invention, it should now be apparent to those skilled in the art that numerous other embodiments and modifications thereof are contemplated as falling within the scope of the present invention, as defined by the appended claims.

What is claimed is:

1. A sheath for covering an intravenous device to shield the device from a patient's skin, said sheath comprising:
   a layer of a soft woven material;
   a thin layer of a plastic material formed on an inner surface of the soft woven material to form, with said soft woven material, a pliable wrap meant to be disposed about the intravenous device for shielding the patient's skin from the intravenous device;
   said pliable wrap having inner and outer surfaces, top and bottom ends, and respective sides;
   an elastic member secured to at least one of said top and bottom surfaces of said pliable wrap to provide a gathered area surrounding the intravenous device at at least one end thereof;
   and a fastening member secured between the respective sides of the pliable wrap to extend in a closed manner about the intravenous device;
   wherein, when the fastening member is secured, the pliable wrap assumes a closed tubular form; and
   wherein the closed tubular pliable wrap is constructed and arranged so that only the soft woven material is exposed to the patient's skin while the thin layer of a plastic material is disposed against the intravenous device;
   wherein the soft woven material comprises one of a cotton flannel and a soft woven wool;
   wherein the soft woven material forms an inner surface of the wrap while the thin layer of a plastic material forms an outer surface of the wrap;
   wherein the thin layer of a plastic material comprises a polyurethane layer having thickness on the order of one mm and has a thickness that is less than the thickness of the layer of a soft woven material;
   wherein the respective sides of said pliable wrap are constructed and arranged as opposed longitudinally extending folds that are disposed in parallel to each other and that each define an outer fold surface;
   wherein the fastening member comprises separate respective elongated hook and loop strips that are adhesively attached to respective outer fold surfaces of the opposed longitudinally extending folds;
   wherein the respective top and bottom ends of said pliable wrap are constructed and arranged as opposed longitudinally extending folds that are disposed in parallel to each other and that each define a fold recess;
   wherein the elastic member comprises respective top and bottom elongated elastic bands each having a length, in its relaxed state, that is less than the width of the pliable wrap, the elastic bands stretched and secured by stitching to an edge at at least one end of the pliable wrap so that each of the elastic bands is secured in place to create a gathering at both the top and bottom of the pliable wrap;
   wherein each of the respective elongated elastic bands is disposed within the respective fold recess so that the respective top and bottom folds are each disposed over respective top and bottom elongated elastic bands;
   wherein the top and bottom folds are formed by heat sealing; and
   wherein the side folds are formed by heat sealing.

2. The sheath of claim 1 wherein each elongated hook and loop strip has a width on the order of ¼ inch.

3. The sheath of claim 1 wherein each elongated elastic band has a thickness in a range of 10 to 20 mm.

4. The sheath of claim 1 wherein the soft woven material is synthetic.

5. The sheath of claim 1 wherein each elongated elastic band has a thickness in a range of 10 to 20 mm; a width on the order of ¼ inch; and a length in a range of 3¼ to 3½ inch.

* * * * *